United States Patent [19]

Taschner et al.

[11] Patent Number: 5,176,884
[45] Date of Patent: Jan. 5, 1993

[54] STERILIZING CONTAINER

[75] Inventors: Wolfgang Taschner, Tuttlingen; Wilfried Wölfle, Bad Dürrheim, both of Fed. Rep. of Germany

[73] Assignee: Aesculap AG, Fed. Rep. of Germany

[21] Appl. No.: 690,993

[22] PCT Filed: Nov. 28, 1989

[86] PCT No.: PCT/EP89/01443
§ 371 Date: Jun. 18, 1991
§ 102(e) Date: Jun. 18, 1991

[87] PCT Pub. No.: WO90/07346
PCT Pub. Date: Jul. 12, 1990

[30] Foreign Application Priority Data
Jan. 3, 1989 [DE] Fed. Rep. of Germany ....... 3900049

[51] Int. Cl.⁵ .................................................. A61L 2/06
[52] U.S. Cl. ..................... 422/292; 422/103; 422/114; 422/295; 422/296; 422/298; 422/299; 422/310; 137/468; 220/201; 220/371; 220/372
[58] Field of Search ........ 422/292, 103, 114, 295–296, 422/298–299, 310; 137/468; 220/201, 371–372

[56] References Cited

U.S. PATENT DOCUMENTS

| 2,024,004 | 12/1935 | Jewell et al. | 422/114 X |
| 2,613,130 | 10/1952 | Jewell et al. | 422/114 |
| 2,715,251 | 8/1955 | Vischer, Jr. | 137/468 |
| 4,416,417 | 11/1983 | Sanderson et al. | 422/310 X |
| 4,457,327 | 7/1984 | Pepper | 422/310 X |
| 4,551,311 | 11/1985 | Lorenz | 422/310 X |

FOREIGN PATENT DOCUMENTS 3438463 4/1986 Fed. Rep. of Germany .

Primary Examiner—Robert J. Warden
Assistant Examiner—Stephanie Blythe
Attorney, Agent, or Firm—Barry R. Lipsitz

[57] ABSTRACT

In a sterilizing container with a perforated zone which can be covered over in relation to the interior of the container by a filter designed so that it can be displaced and covered over, in order to improve the protection of the filter, on the one hand, and the sealing-off of a bypass under different operating conditions, on the other hand, it is proposed that force elements be used for displacing a covering disc of the filter and the filter itself which change the displacement forces acting on the covering disc and on the filter, respectively, as a function of the temperature.

16 Claims, 4 Drawing Sheets

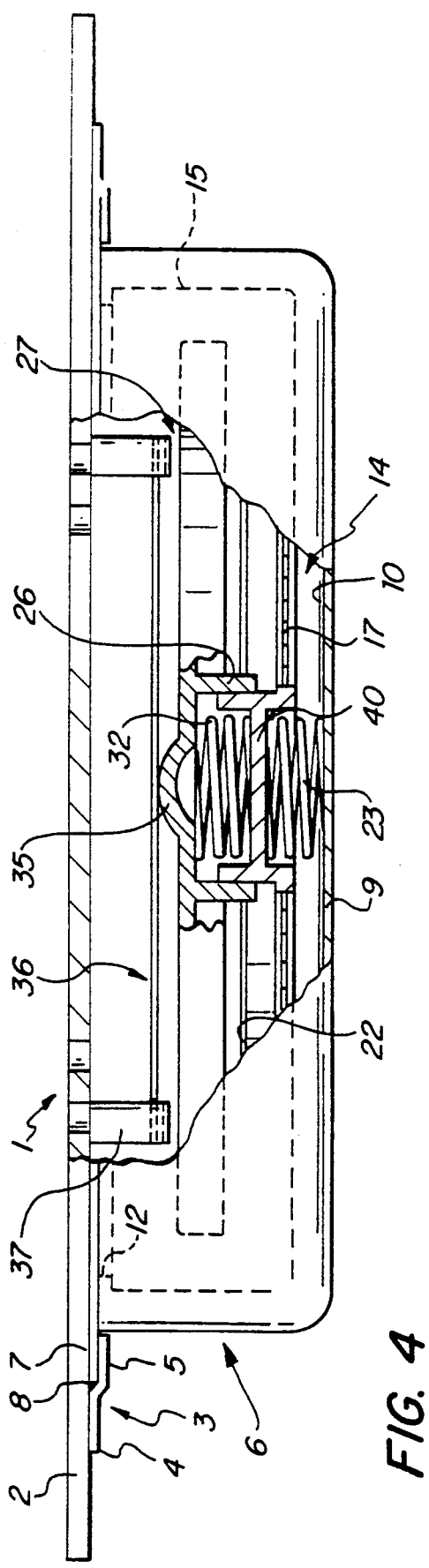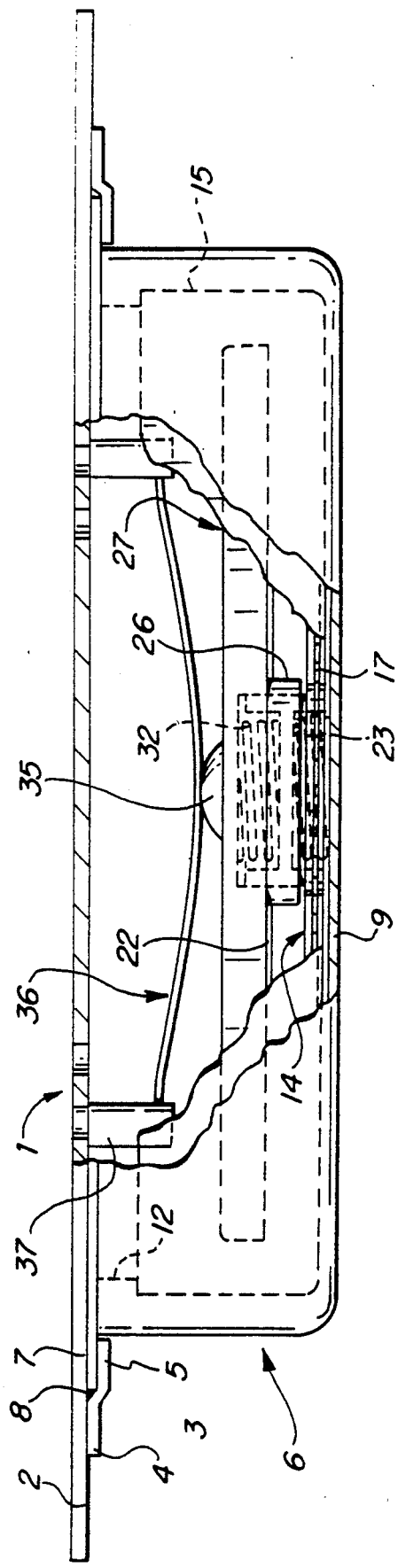

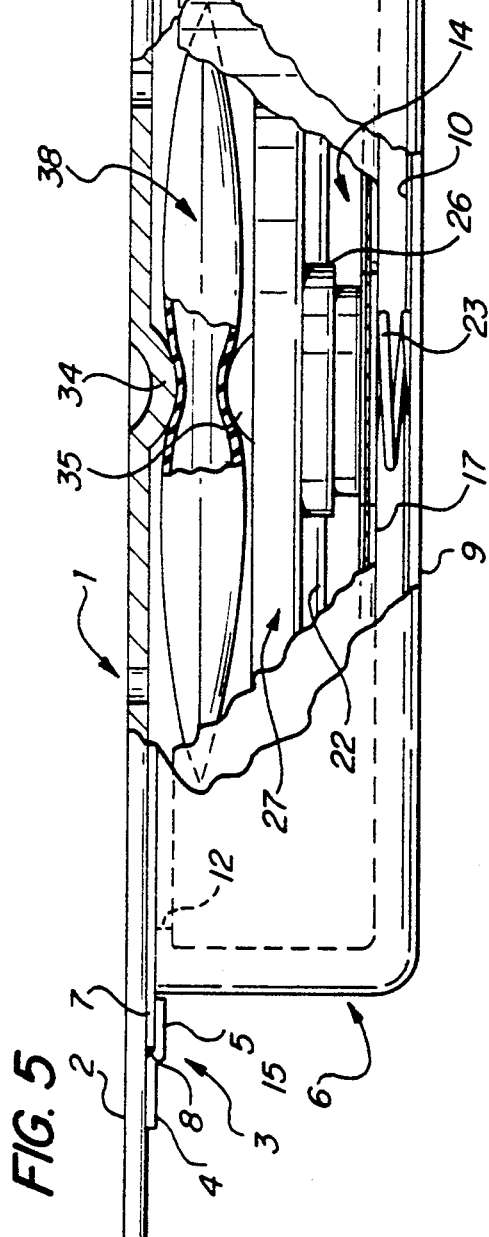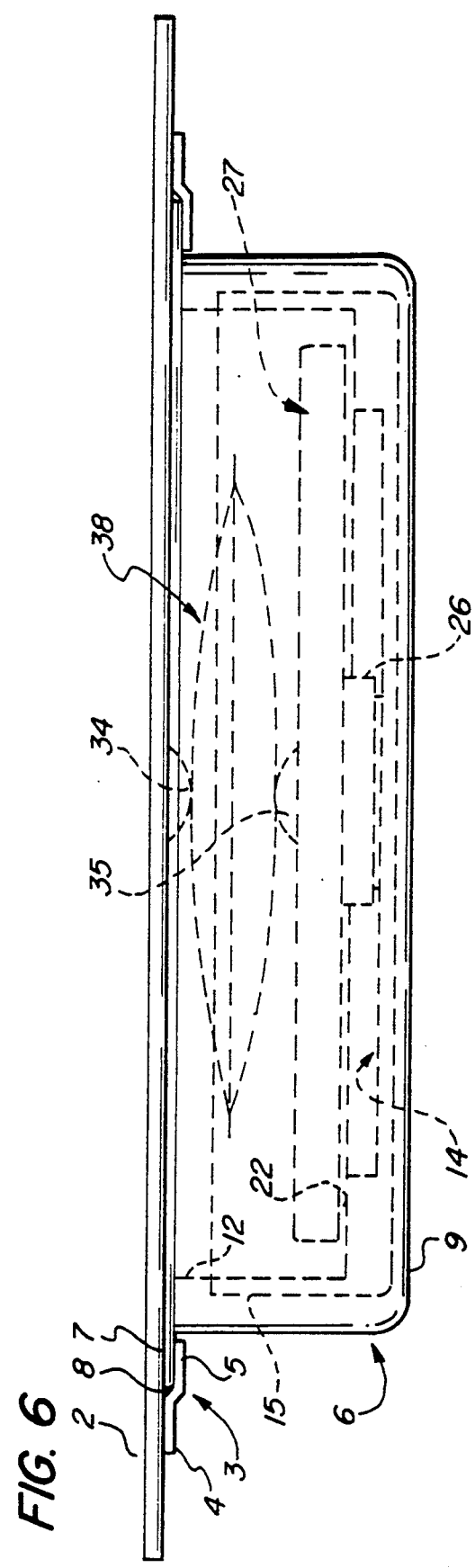

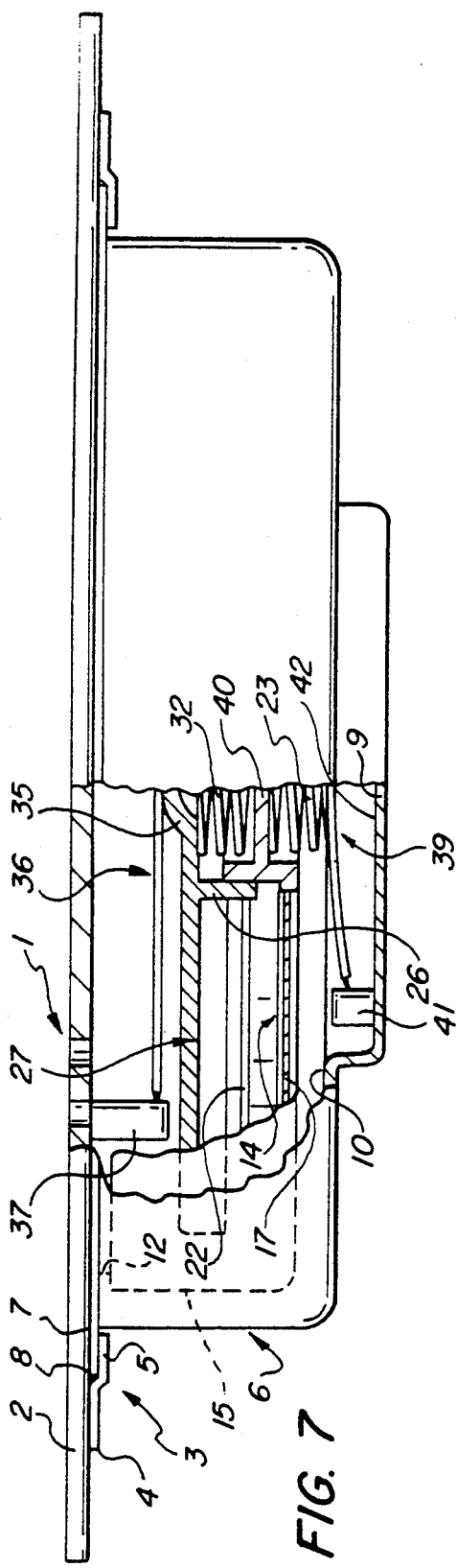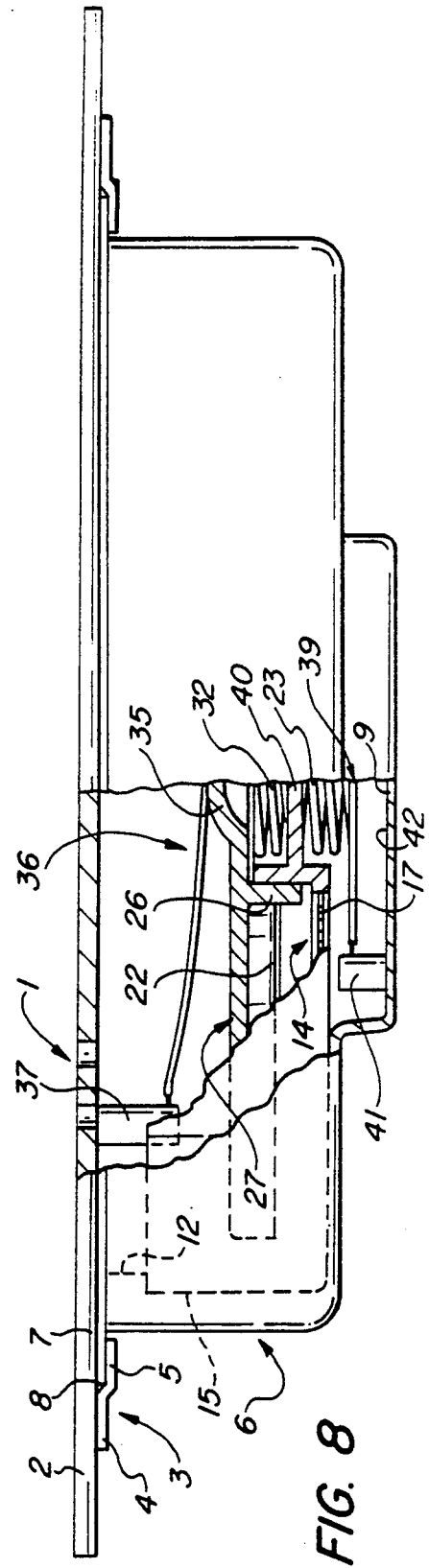

STERILIZING CONTAINER

The invention relates to a sterilizing container with a perforated zone that opens to a filter element having a displaceable protective cover.

Such sterilizing containers have already been proposed (German patent application P 38 38 099.4).

With these specially designed filters, it is normally possible to cover the perforated zone in the wall or the lid of a sterilizing container with the filter layer so a gas exchange can take place through the perforation and the filter layer. Once gas enters the container at a high speed, for example, when the steam flows in for the sterilization, this steam moves the covering disc in the direction towards the filter which is thereby covered on its top side. At the same time, the covering disc resting sealingly on the filter also moves the filter and places it sealingly on the bottom cover. As a result of this, the filter is sealingly covered on both sides and hence completely protected. The movement of the filter itself causes elimination of the sealing of the filter with respect to the perforated zone of the container wall or in the container lid and so the gas exchange can now take place outside the sealed regions without filtration occurring. Accordingly, in this second operating phase, the unit comprised of covering disc, filter and bottom cover is removed from the actual flow path, whereas in the first operating phase the filter lies in the flow path and is free on both sides thereof from covering disc and bottom cover, respectively. In this way, the filter is only connected in the flow path during part of the operating sequence, while in another operating phase in which particularly heavy soiling of the filter is to be feared, the filter is not located in the flow path. This permits substantially longer use of a certain filter while maintaining the same operating safety.

The object of the invention is to further improve such a filter construction such that during normal operation of the sterilizing container, the gas exchange takes place with particularly high reliability via the filter, while during the sterilization, on the other hand, it is ensured that the filter is reliably protected by cover and covering disc and yet the bypass flow path leading past the filter into the container interior is effectively opened.

This object is accomplished in accordance with the invention with a sterilizing container of the kind described at the beginning in that the force elements which subject the covering disc and the filter to displacement forces modify the displacement forces exerted on the covering disc and the filter, respectively, as a function of the temperature.

Hence displacement of the covering disc and the filter is brought about not only by the action of the springs and the pressure thrusts exerted by the inflow of gas or steam but also additionally under the influence of the temperature change during the sterilizing operation which thus additionally promotes the release and enveloping, respectively, of the filter.

In particular, provision may be made for force elements which press the covering disc against the filter to increase the pressing forces as the temperature rises. Furthermore, the force elements which press the filter against the cover may be designed so as to reduce the pressing forces as the temperature rises. As a result of this, at normal ambient temperature the covering disc is more easily lifted off the filter than at high temperatures at which sterilization takes place. In addition, at lower temperatures the contact between the filter and the seals closing the bypass openings is promoted, which increases the reliability of this seal and ensures that at lower temperatures a flow connection will in any case only be possible via the filter.

At higher temperatures, i.e., during the sterilizing operation, however, the temperature-dependent force elements promote the opening of the bypass flow path and the protective enveloping of the filter so the opening of the bypass flow path and the enclosing of the filter are brought about not only by the pressure thrusts of the inflow of steam but already either on account of the increased temperature alone or at increased temperature and upon a relatively low increase in pressure owing to the inflow of steam.

Provision may be made for the force elements to be closed bodies with deformable walls containing a medium which expands as the temperature rises. The bodies may thus be filled with a liquid which evaporates as the temperature increases.

Such bodies can, for example, be of cushion-shaped or bellows-type design.

In a modified embodiment, provision is made for the force elements to consist of memory metal and so at different temperatures the force elements assume a different shape and hence subject covering disc and/or filter to pressing forces in a different way. It is also possible for the force elements to be designed as bimetal elements.

It is expedient for a force element to be arranged between the perforated zone and the covering disc. This force element supports the contacting of the covering disc on the filter and normally counteracts the spring which lifts the covering disc off the filter. This counteraction to the spring force is temperature-dependent and so the spring force is compensated differently as a function of the temperature.

It is, furthermore, expedient for a force element to be arranged between cover and filter, with its effect being the reversal of the effect of a force element between the perforated zone and the covering disc, i.e., this force element between cover and filter promotes at low temperatures the action of the spring which lifts the filter off the cover, at higher temperatures, on the other hand, this promoting component is reduced. In this case, it is advantageous for the spring to be supported between cover and filter on the force element.

BRIEF DESCRIPTION OF THE DRAWINGS

The following description of preferred embodiments serves in conjunction with the drawings to explain the invention in further detail. The drawings show:

FIG. 3: a modified embodiment with a force element made of memory metal when the bypass flow path is closed;

FIG. 4: a view similar to FIG. 3 when the bypass flow path is open;

FIG. 5: a view similar to FIG. 3 in an embodiment with a cushion-shaped force element when the bypass flow path is closed;

FIG. 6: a schematic view similar to FIG. 5 when the bypass flow path is open;

FIG. 7: a modified embodiment of a filter valve with two force elements made of memory metal when the bypass flow path is closed; and FIG. 8: a view similar to FIG. 7 when the bypass flow path is open.

Figure 1:
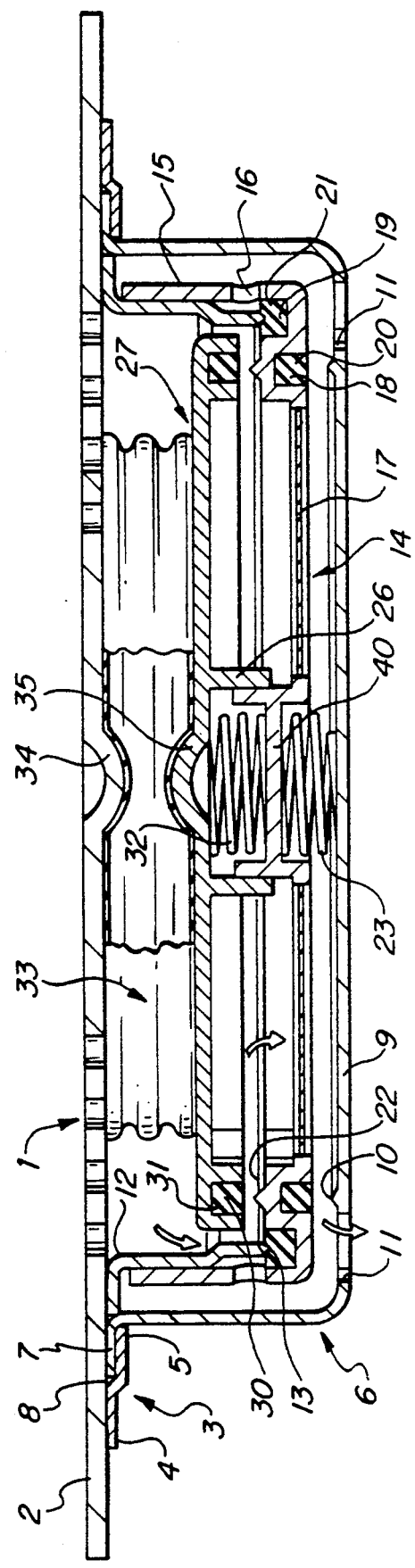
FIG. 1: a cross-sectional view of a filter valve with the filter connected in the flow path and a bellows-type force element between perforated zone and covering disc when the bypass flow path is closed.

The filter valve assembly illustrated in the drawings can, in principle, be arranged on any wall of a sterilizing container which comprises a perforated zone 1. In the given example, the perforated zone 1 is arranged in the top wall 2 of a lid illustrated only partially in the drawings. The perforated zone 1 may, for example, occupy a circular area.

In the illustrated embodiment, this perforated zone 1 is enclosed by a holding strip 3 surrounding the perforated zone 1 over only part of its circumference at a spacing from it. The holding strip 3 comprises a first region 4 in surface-to-surface contact with the wall 2 and held in this region on the wall 2 and a second region 5 directed towards the perforated zone 1, laterally offset in relation to the region 4 and hence maintaining a spacing between itself and the wall 2. A circular-cylindrical housing 6 engages with its radially outwardly bent top rim 7 the space 8 between the region 5 of the holding strip 3 and the wall 2 and so the housing 6 is held in this way on the wall 2. The rim 7 also extends over only part of the circumference of the cylindrical housing 6 and so by turning the housing 6 about the cylinder axis, the rim 7 can be turned out of the space 8 until the housing 6 is removable from the wall 2.

The bottom end face wall 9 remote from the wall 2 is of essentially flat design and closes off the cylindrical housing 6 substantially. The central part of the end face wall 9 is delimited by a sealing rib 10. A large number of openings 11 is provided radially outwardly of the sealing rib 10 along the circumference of the end face wall 9.

The perforated zone 1 is surrounded by a downwardly extending connection piece 12 protruding downwards from the wall 2 with a bottom rim 13 designed as sealing edge.

Arranged above the end face wall 9 which acts as cover is a filter disc 14, the outer, upwardly extending rim 15 of which encloses the outer side of the connection piece 12 and forms together with the connection piece 12 a sliding guide for the filter disc 14 which enables displacement of the filter disc in the vertical direction relative to the end face wall 9. Flow orifices 16 are provided at the sides in the upwardly bent rim 15 of the filter disc 14. These are located in a region in which the connection piece 12 is offset inwardly so the connection piece 12 exhibits a slight radial spacing from the rim 13.

The filter disc 14 carries in the central region a ring-shaped filter 17 which extends in the radial direction approximately as far as the beginning of the sealing rib 10 in the end face wall 9. In the central region of the filter disc 14, the filter 17 extends as far as a central hub 40. The filter can be a metal screen or a glass fiber screen. It can also consist of plastic fibers.

The outer rim of the filter 17 is surrounded by two adjacent annular grooves 18 and 19 which are formed by impression in the filter disc 14. The inner annular groove 18 opens downwards and is located above the sealing rib 10 in the end face wall 9. The outer annular groove 19 directly adjoins the inner annular groove 18 and opens upwards. A silicon seal 20 and 21, respectively, is inserted in each of the two annular grooves 18 and 19. A circumferential sealing edge 22 is arranged on the filter disc 14 directly above the downwardly open annular groove 18.

A helical spring 23 is arranged between end face wall 9 and filter disc 14. It is supported with its bottom part on the end face wall 9 and with its top part on the hub 40. This helical spring 23 displaces the filter disc 14 in the direction towards the wall 2 until the silicon seal 21 in the outer annular groove 19 contacts the bottom rim 13 of the connection piece 12.

In the space enclosed by the connection piece 12 there is a covering disc 27 carrying a downwardly protruding ring wall 26 in its central region. This ring wall 26 encloses the hub 40 in the filter disc 14 and is thereby mounted on the filter disc 14 for displacement in the vertical direction. The covering disc 27 is of essentially flat design without openings. At its outer rim, it carries a downwardly open annular groove 30 which is located exactly above the inner annular groove 18 of the filter disc 14 and likewise receives a silicon seal 31. A further helical spring 32 is arranged between the filter disc 14 and the covering disc 27. It is supported, on the one hand, on the hub 40 and, on the other hand, on the underside of the covering disc 27 and thereby attempts to remove the covering disc from the filter disc.

Figure 2:
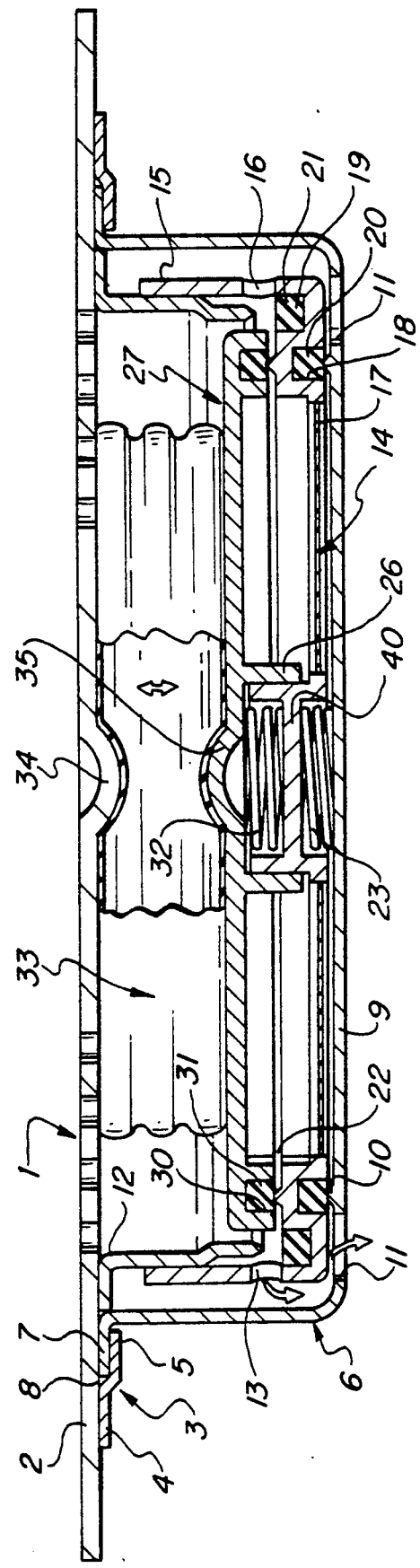
FIG. 2: a view similar to FIG. 1 when the bypass flow path is open.

In the embodiment of FIGS. 1 and 2, a further force element 33 in the form of a bellows is arranged between the perforated zone 1 and the top side of the covering disc 27. It is in surface-to-surface contact with the perforated zone 1 and the top side of the covering disc 27 and is fixed in its position by outwardly bent portions 34 and 35 in the wall 2 and the covering disc 27, respectively. This bellows-type force element 33 is filled with a medium which at ambient temperature is preferably liquid and evaporates when the temperature increases and so the pressure inside the bellows-type force element increases strongly with the rise in temperature. Owing to this pressure increase, the bellows-type force element attempts to expand, i.e., it exerts on the covering disc 27 a force increasing with the temperature which attempts to move the covering disc 27 against the filter disc 14 and against the end face wall 9.

The bellows-type force element 33 can, of course, also be filled with a medium which is already gaseous at ambient temperature. In this case, too, a rise in temperature will be accompanied by a considerable increase in pressure and hence a tendency of the force element to exert an increased displacement force on the covering disc 27 as the temperature increases.

During normal operation, i.e., when the sterilizing container is operated at ambient temperature and there is no strong flow of gas passing through the perforated zone 1 (FIG. 1), the filter disc 14 is sealingly pressed by the bottom helical spring 23 against the bottom rim 13 of the connection piece 12 and the covering disc 27 by the top helical spring 32 upwards against the force element 33. This results in a flow path through the openings of the perforated zone 1, past the outer side of the covering disc 27 into the space between covering disc 27 and filter disc 14. In this case, the flow of gas must pass through the filter 17 of the filter disc 14 as the filter disc 14 is sealingly pressed against the connection piece 12. After passing through the filter, the flow of gas enters the container interior through the openings 11. During the cooling-down of the container contents when a negative pressure develops in the interior, air aspirated in this way from the ambient is reliably cleaned by the filter 17. Also steam still present in the container interior after the sterilization can travel outwards in the reverse direction through the filter 17 without there being any danger of an impurity entering the container interior.

When, on the other hand, the temperature increases considerably or a very great pressure difference develops between outside and inside, resulting in a very strong inwardly directed flow as is, for example, the case when steam flows in at the beginning of the sterilizing operation, the covering disc 27 is thereby displaced in the direction towards the end face wall 9 until its silicon seal 31 sealingly contacts the sealing edge 22 of the filter disc 14 and thus seals off the filter 17 on the top side thereof. At the same time, the covering disc 27 presses the filter disc 14 upon further displacement in the direction towards the end face wall 9 against the outer part of the sealing rib 10 which thereby enters into sealing contact with the silicon seal 20 and hence seals off the filter 17 from the underside thereof (FIG. 2). In this position, the filter is, therefore, enclosed in a sealed-off space by the covering disc 27, on the one hand, and by the end face wall 9 acting as cover, on the other hand, so there is no longer any flow of gas passing through the filter. Instead, the incoming gas travels along the outside of the covering disc 27 and through the flow orifices 16 directly to the openings 11 in the end face wall 9.

The displacement of the covering disc 27 and of the filter disc 14 is promoted by the pressing force of the force element 33 which increases as the temperature rises. In this case, it is possible by way of suitable dimensioning for the effect of the displacement force of the force element 33 increasing as a function of the temperature, on the one hand, and the displacement forces caused by the flow of gas, on the other hand, to be attuned to one another such that depending on what is desired, displacement in accordance with FIG. 2 will always occur either at an increased temperature or only when promoted by a certain pressure difference caused by a flow of gas.

When a force element with contents which are liquid at ambient temperature is used, it is additionally advantageous for a very strong increase in pressure to occur at a certain temperature during the transition to the vapor phase so it is thereby possible for the displacement forces to be kept relatively low below a certain temperature but for them to be allowed to increase very strongly when a certain temperature within a small temperature range is exceeded.

The embodiment illustrated in FIGS. 3 and 4 corresponds substantially to that of FIGS. 1 and 2 and corresponding parts, therefore, have the same reference numerals.

Differently from the embodiments of FIGS. 1 and 2, the force element 33 in the form of a bellows is replaced in the embodiment of FIGS. 3 and 4 by a strip-shaped force element 36 which extends between two supports 37 and rests directly on the bent-out portion 35 of the covering disc 27. In this embodiment, the strip-shaped force element 36 consists of a memory metal alloy with a temperature-dependent shape memory. At low temperatures, this force element 36 extends between the two supports 37 substantially parallel to the covering disc 27. At increased temperatures, on the other hand, this force element 36 bends downwards in the direction towards the covering disc 27 in the manner shown in FIG. 4 and thereby acts on the covering disc 27 with an additional force counteracting the helical spring 32. This change in shape of the force element 36 is temperature-dependent and reversible and so in a similar way as with the bellows-type force element 33, this force element 36 brings about as a function of the temperature an increase and a decrease, respectively, in the displacement forces acting on the covering disc 27. The force element 36 may be designed such that when a certain temperature is reached, the change in shape brings about a tilting effect, i.e., the force element 36 snaps from a first into a second position and thereby abruptly brings about a change in the displacement forces acting on the covering disc 27 when this temperature is exceeded. This abrupt change in the displacement forces can take place at different temperatures as the temperature rises and as the temperature drops, i.e., an hysteresis effect can be used in addition.

The embodiment illustrated in FIGS. 5 and 6 in which corresponding parts again have the same reference numerals corresponds substantially to that of FIGS. 1 and 2. The bellows-type force element 33 illustrated therein is replaced in the embodiment of FIGS. 5 and 6 by a cushion-shaped force element 38 which is fixed in its position in a similar way as the bellows-type force element 33 and is likewise filled with a medium which greatly changes the pressure in the interior of the deformable cushion as a function of the temperature. The function, therefore, likewise corresponds to that of the embodiments of FIGS. 1 and 2.

In the embodiment of FIGS. 7 and 8 which corresponds substantially to that of FIGS. 3 and 4 and in which corresponding parts have the same reference numerals, the bottom helical spring 23 is not supported directly on the end face wall 9 but on a further force element 39 which like the force element 36 is made of a memory metal alloy. This force element 39 s held between two supports 41 which, for their part, are located in a recessed central region 42 of the end face wall 9. In contrast with the force element 36, this force element 39 is bent out at low temperature, more specifically, in the direction towards the top wall 2 and so at low temperatures the pressing force exerted by the bottom helical spring 23 on the filter disc 14 is increased. With a rise in temperature, the force element 39 changes to a position in which it extends substantially parallel to the filter disc 14 and so the bottom supporting point of the helical spring 23 is moved away from the filter disc 14, i.e., the upwardly directed displacement force on the filter disc 14 is reduced.

In this way, at low temperatures the filter disc 14 is pressed with a greater force against the bottom rim 13 of the connection piece 12, which increases the reliability of the covering in this region. When the temperature is increased, this additional pressing force owing to the deformation of the force element 39 is eliminated and so displacement of the filter disc 14 against the end face wall 9 is facilitated.

The use of two temperature-dependent force elements results, on the one hand, in a particularly reliable sealing at ambient temperatures, i.e., during the nonsterilizing operation, and, on the other hand, the opening of the bypass and the safe covering of the filter particularly at the beginning of the sterilizing operation are considerably facilitated.

In the embodiments of FIGS. 3 and 4 and of 7 and 8, respectively, the force elements can, of course, also be in the form of bimetal elements. In the embodiment of FIGS. 7 and 8, it is also possible to replace the bottom force elements 39 by bellows-type or cushion-shaped force elements but these would then have to become effective via a deviation of force as they reinforce the force of the helical spring 23 at low temperatures but must be as ineffective as possible at high temperatures.

We claim:

1. Filtering apparatus for a sterilizing container comprising:

a filter chamber;

a filter enclosed by said filter chamber and mounted for sliding displacement toward a sealing surface of said chamber;

an input zone in said filter chamber for allowing the entry of a sterilizing medium into the chamber;

an output zone in said filter chamber for allowing the exit of said sterilizing medium;

a covering member mounted within said chamber between said filter and one of said input and output zones for sliding displacement toward said filter; wherein said covering member sealingly contacts a sealing portion of said filter and said filter sealingly contacts the sealing surface of said chamber in response to a displacement of said covering member and filter;

means for biasing said covering member away from said filter element and said filter away from the sealing surface of said chamber to provide a filtered flow path between said input zone and said output zone;

means, responsive to the displacement of at least one of said covering member and filter, for opening an auxiliary flow path between said input zone and said output zone while closing said filtered flow path when said covering member is in sealing contact with said filter and said filter is in sealing contact with the sealing surface of said chamber; and means responsive to a change in temperature for facilitating the displacement of said covering member into sealing contact with said filter and said filter into sealing contact with the sealing surface of said chamber.

2. Apparatus in accordance with claim 1 wherein said temperature responsive means are mounted to bear upon said covering member to provide an increasing force to displace said covering member toward said filter as the temperature rises.

3. Apparatus in accordance with claim 2 wherein said means for biasing said filter away from the sealing surface of said chamber are mounted between said filter and said sealing surface for providing a decreasing force as the temperature rises.

4. Apparatus in accordance with claim 1 wherein said means for biasing said filter away from the sealing surface of said chamber are mounted between said filter and said sealing surface for providing a decreasing force as the temperature rises.

5. Apparatus in accordance with claim 1 wherein said temperature responsive means comprise:

closed bodies having deformable walls; and a medium contained in said closed bodies that expands with an increase in temperature.

6. Apparatus in accordance with claim 5 wherein said medium comprises a liquid that evaporates with an increase in temperature.

7. Apparatus in accordance with claim 5 wherein said closed bodies are cushion shaped.

8. Apparatus in accordance with claim 5 wherein said closed bodies comprise bellows.

9. Apparatus in accordance with claim 1 wherein said temperature responsive means comprise memory metal.

10. Apparatus in accordance with claim 2 wherein said temperature responsive means comprise memory metal.

11. Apparatus in accordance with claim 1 wherein said temperature responsive means comprise a bimetallic element.

12. Apparatus in accordance with claim 2 wherein said temperature responsive means comprise a bimetallic element.

13. Apparatus in accordance with claim 1 wherein at least a portion of said temperature responsive means are mounted between said covering member and said one of said input and output zones.

14. Apparatus in accordance with claim 1 wherein at least a portion of said temperature responsive means are mounted between said filter and the sealing surface of said chamber.

15. Apparatus in accordance with claim 14 wherein said means for biasing said filter away from the sealing surface of said chamber comprises a spring supported on said portion of said temperature responsive means.

16. Apparatus in accordance with claim 1 wherein:

said input zone comprises perforations in a first wall of said chamber;

said output zone comprises at least one opening in a second wall of said chamber; and said covering member is mounted between said input zone and said filter.

* * * * *